United States Patent
Barkóczy et al.

Patent Number: 5,225,410
Date of Patent: Jul. 6, 1993

[54] TRIAZOLYL HYDRAZIDE DERIVATIVES

[75] Inventors: József Barkóczy; József Reiter; László Pongó; Lujza Petocz; Frigyes Görgényi; Márton Fekete; Enikó Szirt née Kiszelly; Mária Szécsey née Hegedus; István Gacsályi; István Gyertyán, all of Budapest, Hungary

[73] Assignee: Egis Gyogyszergyar, Budapest, Hungary

[21] Appl. No.: 604,488

[22] Filed: Oct. 25, 1990

[30] Foreign Application Priority Data

Oct. 25, 1989 [HU] Hungary .............................. 5428/89

[51] Int. Cl.$^5$ .................. A61K 31/535; C07D 413/04
[52] U.S. Cl. .................................. 514/236.2; 544/132
[58] Field of Search ...................... 544/132; 514/236.2

[56] References Cited

U.S. PATENT DOCUMENTS 5,021,081  6/1991  Findeisen et al. ................ 548/264.8

OTHER PUBLICATIONS

Rudnicka et al, "Derivatives of 3-amino-1,2-,4-kiazole", etc CA87:5871r (1976).

*Primary Examiner*—Patricia L. Morris
*Attorney, Agent, or Firm*—Beveridge, DeGrandi, Weilacher & Young

[57] ABSTRACT

This invention relates to novel triazolyl hydrazide derivatives and a process for the preparation thereof.

The new triazolyl hydrazide derivatives of the general formula (I).

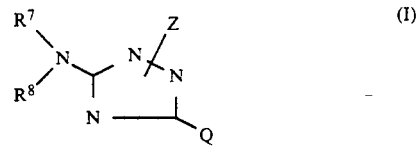

wherein

Q represents hydrogen or a heterocyclic group optionally substituted by a $C_{1-4}$ alkyl group; or a group of general formula $SR^1$, wherein $R^1$ stands for $C_{1-4}$ alkyl or phenyl-($C_{1-4}$ alkyl) optionally substituted by halogen, $C_{1-4}$ alkyl or nitro substitute therefor substituents; or Q represents a group of the formula $NR^2R^3$, wherein $R^2$ and $R^3$ each represents hydrogen, straight or branched chain $C_{1-6}$ alkyl or $C_{2-6}$ alkenyl;

Z represents hydrogen or a group of the formula $(C=X)-(N-R^4)-NR^5R^6$, wherein X stands for oxygen or sulfur, $R^4$, $R^5$ and $R^6$ each stand for hydrogen or $C_{1-4}$ alkyl;

$R^7$ stands for hydrogen, $C_{1-4}$ alkyl or phenyl-($C_{1-4}$ alkyl) optionally substituted by one or more halogen atom(s) or an amino group optionally substituted by one or two $C_{1-4}$ alkyl substituents, $R^8$ stands for hydrogen or a group of the formula $-(C=X)-(N-R^4)-NR^5R^6$, wherein X, $R^4$, $R^5$ and $R^6$ are as stated above, with the proviso that if Z represents a group of the formula $-(C=X)-(N-R^4)-NR^5R^6$, $R^8$ stands for hydrogen, and if Z represents hydrogen, $R^8$ stands for a group of the formula $(C=X)-(N-R^4)-NR^5R^6$, and pharmaceutically acceptable acid addition salts thereof excert valuable antianginal and/or gastric ulcer inhibiting properties and are useful in therapy.

4 Claims, No Drawings

TRIAZOLYL HYDRAZIDE DERIVATIVES

This invention relates to novel triazolyl hydrazide derivatives, a process for the preparation thereof, pharmaceutical compositions comprising the same, to the use of them for the treatment of diseases and also for the preparation of pharmaceutical compositions suitable for the treatment of said diseases.

According to an aspect of the present invention there are provided new triazolyl hydrazide derivatives of the general formula (I) and pharmaceutically acceptable acid addition salts thereof,

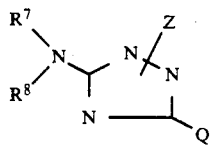

wherein

Q represents hydrogen or a heterocyclic group optionally substituted by a $C_{1-4}$ alkyl group; or a group of general formula $SR^1$, wherein $R^1$ stands for $C_{1-4}$ alkyl or phenyl-($C_{1-4}$ alkyl) optionally substituted by halogen, $C_{1-4}$ alkyl or nitro substitute therefor substituents; or Q represents a group of the formula $NR^2R^3$, wherein $R^2$ and $R^3$ each represents hydrogen, straight or branched chain $C_{1-6}$ alkyl or $C_{2-6}$ alkenyl;

Z represents hydrogen or a group of the formula $(C=X)-(N-R^4)-NR^5R^6$, wherein X stands for oxygen or sulfur, $R^4$, $R^5$ and $R^6$ each stand for hydrogen or $C_{1-4}$ alkyl;

$R^7$ stands for hydrogen, $C_{1-4}$ alkyl or phenyl-($C_{1-4}$ alkyl) optionally substituted by one or more halogen atom(s), or an amino group optionally substituted by one or two $C_{1-4}$ alkyl substituents, $R^8$ stands for hydrogen or a group of the formula $-(C=X)-(N-R^4)-NR^5R^6$, wherein X, $R^4$, $R^5$ and $R^6$ are as stated above, with the proviso that if Z represents a group of the formula $-(C=X)-(N-R^4)-NR^5R^6$, $R^8$ stands for hydrogen, and if Z represents hydrogen, $R^8$ stands for a group of the formula $(C=X)-(N-R^4)-NR^5R^6$.

The invention encompasses all the isomers or tautomeric forms of the compounds of the general formula (I).

The new compounds according to the present invention exhibit excellent biological activity and low toxicity, e.g. they possess antianginal, tranquillant-sedative, cardiovascular, acid secretion inhibiting, gastric ulcer inhibiting and antimicrobial properties and they can be used as starting materials of other pharmaceutically active derivatives as well.

The term "heterocyclic group" used throughout the specification relates to 4 to 8 membered heterocyclic groups which can be formed from compounds comprising independently one or more nitrogen and/or oxygen atom(s) or a group which can be obtained by condensing the same compounds with each other or with benzene. Such groups may be aromatic or partially or completely saturated and may carry one or more substituent(s).

As examples for such groups e.g. the piperidyl, morpholinyl, piperazinyl, furyl, imidazolyl, pyridyl, pyrimidinyl, pyrrolyl, pyrazolyl, pyridazinyl, isoxazolyl, pyrrolinyl, pyrrolidinyl, imidazolidinyl, imidazolinyl, pyrazolidinyl, pyrazolinyl, pyranyl or delta-3-piperidinlyl groups are mentioned.

The term "alkyl group" relates to straight or branched chained saturated aliphatic hydrocarbon groups comprising 1 to 4 or 1 to 6 carbon atom(s), e.g. methyl, ethyl, i-butyl, t-butyl, n-hexyl, etc.

As "$C_{2-6}$ alkenyl" groups straight or branched chained alkenyl groups are mentioned (e.g. vinyl, allyl, 2-methyl-allyl, 1-propenyl, 2-propenyl, 1-butenyl, 2-butenyl, 2-pentenyl, 2-hexenyl etc.).

The term "halogen" emcompasses the fluorine, chlorine, bromine and iodine atoms.

Compounds of the general formula (I), wherein Q represents morpholino, methylthio, dimethylamino or N-methyl-piperazinyl and $R^7$ and $R^8$ each stand for hydrogen, and pharmaceutically acceptable acid addition salts thereof possess particularly valuable pharmaceutical properties.

Particularly preferred representatives of the compounds of the general formula (I) are the following derivatives:

1-(5-amino-3-morpholino-1$\underline{H}$-1,2,4-triazol-1-yl)-N-methylcarbo-thiohydrazide, 1-(5-amino-3-methylthio-1$\underline{H}$-1,2,4-triazol-1-yl)carbothiohydrazide, 1-(5-amino-3-N-methylpiperazinyl-1$\underline{H}$-1,2,4-triazol-1-yl)carbothiohydrazide, 1-(5-amino-3-morpholino-1$\underline{H}$-1,2,4-triazol-1-yl)-N,N'-dimethyl-carbothiohydrazide, and pharmaceutically acceptable acid addition salts thereof.

The compounds of the general formula (I) are organic bases, so they can be transformed into acid addition salts. The pharmaceutically acceptable acid addition salts of the compounds of the general formula (I) can be formed with inorganic or organic acids. As examples for the pharmaceutically acceptable acid addition salts the hydrohalides (such as hydrochlorides or hydrobromides), carbonates, sufates, acetates, fumarates, maleates, citrates, ascorbinates and tartrates can be mentioned.

According to a further aspect of the present invention there is provided a process for the preparation of compounds of the general formula (I) and pharmaceutically acceptable acid addition salts thereof, with comprises a) reacting a triazolyl ester of the general formula (II),

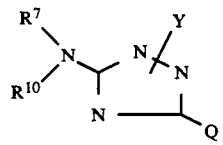

wherein

Y represents hydrogen or a group of the formula $(C=X)-XR^9$, wherein X is as stated above, $R^9$ is $C_{1-4}$ alkyl or phenyl optionally substituted by one or more halogen atom(s), $R^7$ and Q are as defined above, $R^{10}$ represents hydrogen or a group of the formula $(C=X)-XR^9$, with the proviso that if Y stands for hydrogen, $R^{10}$ represents a group of the formula $(C=X)-XR^9$, wherein X and $R^9$ are as stated above, and if Y stands for a group of the formula $(C=X)-XR^9$, $R^{10}$ represents hydrogen, with a hydrazine derivative of the general formula (III),

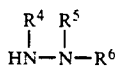

wherein $R^4$, $R^5$ and $R^6$ are as stated above, or b) for the preparation of isomeric compounds of the general formulae (Ib), (Ic) and (Id) representing subgroups of the compounds of the general formula (I),

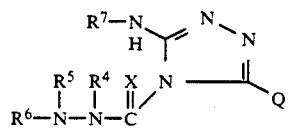

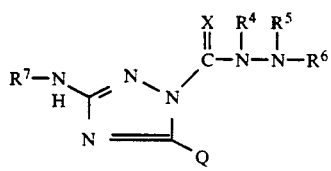

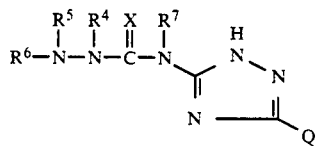

reacting a triazolyl ester of the general formula (IIa),

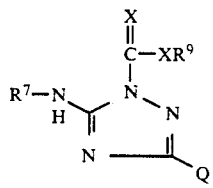

wherein $R^7$, $R^9$, X and Q are as stated above, with a hydrazine derivative of the general formula (III), heating the thus-obtained compound of the general formula (Ia),

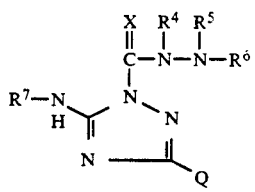

and separating the isomers from each other by methods known per se; or c) for the preparation of isomeric compounds of the general formulae (Ib), (Ic) and (Id) representing subgroups of the compounds of the general formula (I), heating a compound of the general formula (Ia) and separating the isomers from the thus-obtained product by methods known per se; or d) for the preparation of compounds of the general formula (Ia) representing a subgroup of the compounds of the general formula (I), wherein $R^4$, $R^5$, $R^6$ and $R^7$ represent hydrogen and Q stands for a group of the formula $SR^{11}$, wherein $R^{11}$ denotes $C_{1-4}$ alkyl or phenyl-($C_{1-4}$ alkyl) optionally bearing one or more halogen, $C_{1-4}$ alkyl or nitro substituent(s), reacting a compound of the general formula (IV),

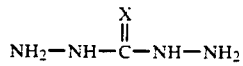

wherein X is as stated above, with a compound of the general formula (V),

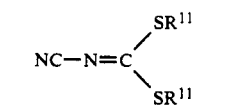

wherein $R^{11}$ is as stated above; and, if desired, converting the compound of the general formula (I) thus-obtained into a pharmaceutically acceptable acid addition salt thereof or setting free a base of the general formula (I) from an acid addition salt thereof, or converting an acid addition salt of a base of the general formula (I) into another acid addition salt.

The reaction of the compounds of the general formulae (II) and (IIa), respectively, with hydrazine derivatives of the general formula (III) is carried out in a solvent inert toward the reactants. For this purpose preferably methanol, 2-propanol, benzene or dimethyl sulfoxid are used. The reaction is performed at a temperature of 0° to 190° C., preferably between 20° and 110° C. The reaction is optionally carried out in the presence of a base, preferably an organic base.

The isomerisation of the compounds of the general formula (Ia) into compounds of the general formulae (Ib), (Ic) and (Id) can be carried out in melt or by thermic rearrangement in a polar or dipolar aprotic solvent, preferably in acetic acid or dimethylformamide, at a temperature between 50° C. and 250° C., preferably at a temperature of 100° to 190° C. During the reaction a mixture of the compounds of the general formulae (Ib), (Ic) and (Id) is produced, which can be separated into the individual isomers by methods known per se, e.g. by chromatography or fractional crystallization.

The reaction of the compounds of the general formulae (IV) and (V) can be performed in a polar solvent, preferably in an aqueous methanol solution, dimethylformamide or dimethyl sulfoxide, at a temperature between 0° and 190° C., preferably at a temperature of 50° to 160° C.

The compounds of the general formula (I) obtained in form of a base can be converted into acid addition salts by methods known per se. For this purpose the free bases are reacted with the corresponding acid in an inert solvent.

The triazolyl esters of the general formula (II) used as starting materials are known compounds or can be produced on the analogy of known compounds (U.S. Pat. No. 3,686,301, DD patent specification No. 105,897).

The hydrazine derivatives of the general formula (III) are also known compounds (Belsteins Handbuch der Organischen Chemie 4, 546, Verlag Springer, Berlin, 1922; Ullmann: Encyklopädie der Technischen Chemie 13, p. 95, Verlag Chemie Weinheim, 1977).

The carbohydrazide and thiocarbohydrazide of the general formula (IV) are commercially available products.

The compounds of the general formula (V) are also commercial products or can be prepared as described in Hungarian patent specification No. 184,743.

The compounds of the general formula (I) are only very slightly toxic and show excellent biological properties. They exert antianginal, tranquillant-sedative, cardiovascular, acid secretion inhibiting, gastric ulcer inhibiting and antimicrobial effects.

The activity of the compounds of the general formula (I) has been examined by the following tests.

1. Antianginal Effect

Method: Nieschulz, E., Popendiker, K. and Hoffmann, I., Arzneimittel-Forschung, 5, 680 (1955)

The test was carried out on rats weighing 180 to 220 g. The animals were narcotised with chloralese-urethane (70–700 mg/kg ip.). The ECG was registered with needle electrodes in standard II leading. The experimental coronaria insufficiency was induced with vasopressin (1 NE/kg i.v.). The height of wave T was measured before and after the administration of vasopressin in both the control and treated groups. Test compounds were administered intravenously 2 minutes prior to the treatment with vasopressin. The results are summarized in Table I.

TABLE I

| Antianginal effect | |
|---|---|
| Test compound (Example No.) | $ED_{50}$ mg/kg (iv.) |
| 17 | 0.84 |
| 16 | 0.70 |
| Prenylamine | 6.5 |

2. Motility Inhibiting Activity

Method: Borsy, J., Csányi, E., Lázár, I.: Arch. Int. Pharmacodyn. 124, 1-2 (1960)

The tests were performed on mice. Groups consisting of 3 mice each were trated perorally with different doses of the compounds to be tested. One hour after the administration the test animals were placed in a Dews equipment. In this equipment the number of interruptions of infrared beam within 30 minutes was counted. The results obtained are shown in Table II.

TABLE II

| Motility inhibiting effect | | |
|---|---|---|
| Compound (Example No.) | $LD_{50}$ mg/kg p.o. | Therapeutical index |
| 1 | 100 | >10 |
| 17 | 70 | ~5 |
| Meprobamate | 270 | 4.1 |

3. Acute toxicity on mice

Method: Litchfield, J. T., Wilcoxon, F. W.: Pharmacol. Exp. Ther., 96, 99 (1949)

White mice belonging to the CFLP strain (body weight 18 to 22 g, both male and female) were used, 6 animals for each dose. The test compounds were administered orally in a volume of 20 ml/kg. After treatment the animals were observed for a period of 14 days. The mice were kept in a plastic cage at room temperature. The animals get tap water and standard mouse fodder ad libitum. The toxicity data were determined with the aid of the method of Litchfield and Wilcoxon. The results are summarized in Table III.

TABLE III

| Acute toxicity on mice | |
|---|---|
| Example No. | $Ld_{50}$ mg/kg p.o. |
| 17 | 350 |
| 16 | 1000 |
| 1 | >1000 |
| 4 | 300 |
| 9 | 1000 |
| 20 | 1000 |

The above data show that certain representatives of the compounds according to the invention are 8 or 10 times as effective on the antianginal test as the reference substance Prenylamine and are superior as motility inhibitors to the reference compound Meprobamate. At the same time they are only very slightly toxic.

In addition, the compounds according to the invention posses valuable antimicrobial effect, especially against nonfermenting Gram-negative bacteria strains. So the compound of Example 9 inhibits, determined by agar diffusion method in a concentration of 500/μg/hole, the bacteria strains listed in Table IV.

TABLE IV

| Antimicrobial effect of the compound according to Ex. 9 | | |
|---|---|---|
| Microbe strain | HNCMB+ deposition number | Inhibition (%) |
| Salmonella enteritidus | 10091 | 17 |
| Shigella sonnei | 20046 | 19 |
| Acinetobacter calcoaceticus | 150001 | 20 |
| Pseudomonas aeruginosa | 170006 | 14 |
| Pseudomonas stutzeri | 173008 | 25 |
| Alcaligenea faecalis | 140001 | 23 |

HNCMB+ = Hungarian National Collection of Medical Bacteria

4. Stomach-Secretion and Ulcus tests on Mice

Method: Shay, H., Komarov, S. A., Fels. S. S., Meranze, D., Gruenstein, M., Siplet, H.: Gastroenterology 5, 45 (1945); Adami, E., Marazzi-Ubertti, E., Tirba, C.: Arch. Int. Pharmacodyn. 147, 113 (1964)

Starved wistar mice of 150-250 g body weight were used, 4 male and 4 female animals for each dose. On the day of the experiment the pylorus of the animals was ligatured under ether narcosis. The doses of the test compounds were administered per os, 3 hours before the operation. The control groups were treated with the carrier in identical way. 4 hours after the operation the animals were over-narcotized with ether, their stomach was removed, the stomach contents were separated and after centrifugation the volume of the gastric juices was measured, then their free-acid content and total acidity, resp., were determined by titration with 0.1N NaOH solution. The changes of the gastric mucous membrane were investigated macroscopically and characterized by an ulcus index determined with the aid of the punctuation method of Adami and coworkers.

The results obtained are shown in Table V.

TABLE V

Gastric-secretion- and ulcus-inhibiting effects of mice

| Example No. | Dose mg/kg po. | Inhibition related to the control in % | | | |
|---|---|---|---|---|---|
| | | Gastric juice | Free acid | Total acidity | Ulcus index |
| 4 | 60 | 41 | 60 | 50 | 67 |
| 20 | 50 | 36 | 46 | 36 | 39 |
| | 200 | 58 | 91 | 78 | 70 |
| Cimetidine | 50 | 22 | 24 | 15 | 18 |
| | 200 | 59 | 91 | 71 | 72 |

The above data unambiguously show that the effect of the compounds according to the invention reach or even surpasse that of Cimetidine but their toxicity is slight and due to the differing structures they are exempt from the very unfavourable side-effect of causing impotency of Cimetidine.

According to a further aspect of the present invention there are provided pharmaceutical compositions comprising as active ingredient at least one compound of the general formula (I) or a pharmaceutically acceptable acid addition salt thereof in admixture with suitable inert solid or liquid pharmaceutical carriers.

The pharmaceutical compositions of the present invention can be prepared by methods known per se by admixing the active ingredient with suitable inert solid or liquid carriers and bringing the mixture to galenic form.

The pharmaceutical compositions of the present invention may be suitable for oral (e.g. tablet, pill, coated pill, dragée, solid or soft gelatine capsule, solution, emulsion or suspension), parenteral (e.g. injection solution) or rectal (e.g. suppository) administration.

As carrier for the preparation of tablets, coated tablets, dragées and solid gelatine capsules e.g. lactose, corn starch, potatoe starch, talc, magnesium carbonate, magnesium stearate, calcium carbonate, stearic acid or the salts thereof, etc. can be used. As carrier for the soft gelatine capsules e.g. vegetable oils, fats, waxes or polyols of suitable consistency can be used. As carriers for the solutions and syrups e.g. water polyols (polyethylene glycol), saccharose or glucose can be used. The injection solutions can comprise e.g. water alcohols, polyols, glycerol or vegetable oils as carrier. The suppositories can be prepared with the aid of e.g. oils, waxes, fats or polyols of suitable consistency.

In addition, the pharmaceutical formulations may comprise auxiliaries usually applied in pharmaceutical industry, e.g. wetting, sweetening agents, aroma substances, salts causing the change of osmotic pressure, buffers, etc.

The compounds of the general formula (I) can preferably be used in therapy orally in the form of tablets or capsules. Especially preferred are the capsules or tablets comprising 0.5 to 500 mg of active ingredient.

The daily dose of the compounds of the general formula (I) can vary within wide ranges depending on several factors, e.g. on the activity of the active ingredient, the patient's condition and age, the severity of the disease, etc. The oral dose is generally 2 to 5000 mg/day, preferably 5 to 1000 mg/day. It has to be stressed that the above dose is only of informative character and the administered dose must always be determined by the physician therapeutist.

According to a further aspect of the present invention there is provided the use of the compounds of the general formula (I) or pharmaceutically acceptable salts thereof for the preparation of pharmaceutical compositions having particularly antianginal and/or gastric ulcer inhibiting effects.

According to a still further aspect of the present invention there is provided a method for antianginal and/or gastric ulcer inhibiting treatment, which comprises administering to the patient an effective amount of a compound of the general formula (I) or a pharmaceutically acceptable salt thereof.

The invention is further illustrated by the aid of the following Examples of non-limiting character.

EXAMPLE 1

1-(5-Amino-3-morpholino-1H-1,2,4-triazol-1-yl)-N-methyl-carbothiohydrazide 25.7 g (0.1 mole) of methyl (5-amino-3-morpholino-1H-1,2,4-triazol-1-yl)carbodithioate are stirred in 150 ml of methanol, in the presence of 6.9 ml (0.13 mole) of methylhydrazine for 4 hours at room temperature. Then the separated crystals are filtered off and recrystallized from benzene.

Yield: 15.0 g (59%)
M.p.: 144° to 146° C.

EXAMPLE 2

1-(5-Amino-3-morpholino-1H-1,2,4-triazol-1-yl)-N'-methyl-carbothiohydrazide

One proceeds as described in Example 1, with the difference that the mother liquor obtained after filtering the reaction mixture is allowed to stand for 2 days. The separated crystals are then filtered off and recrystallized from 2-propanol.

Yield: 3.8 g (15%)
M.p.: 125° to 126° C.

EXAMPLE 3

1-(5-Amino-3-morpholino-1H-1,2,4-triazol-1-yl)-N-methyl-carbothiohydrazide 25.7 g (0.1 mole) of methyl (5-amino-3-morpholino-1H-1,2,4-triazol-1-yl)carbodithioate are stirred in 100 ml of dimethyl sulfoxide, in the presence of 5.7 ml (0.11 mole) of methylhydrazine for 8 hours at room temperature. The reaction mixture is poured onto 100 ml of water, the separated crystals are filtered off and recrystallized from benzene.

Yield: 8.3 g (38%)
M.p.: 144° to 146° C.

EXAMPLE 4

EXAMPLE 4

1-(5-Amino-3-methylthio-1H-1,2,4-triazol-1-yl)-N-methyl-carbothiohydrazide 22.0 g (0.1 mole) of methyl (5-amino-3-methylthio-1H-1,2,4-triazol-1-yl)carbodithioate are stirred in 150 ml of methanol, in the presence of 6.9 ml (0.13 mole) of methylhydrazine for 4 hours at room temperature. The separated crystals are filtered off and recrystallized from benzene.

Yield: 11.8 g (54%)
M.p.: 164° to 166° C.

EXAMPLE 5

1-(5-Amino-3-methylthio-1H-1,2,4-triazol-1-yl)-N-methyl-carbothiohydrazide 22.0 g (0.1 mole) of methyl (5-amino-3-methylthio-1H-1,2,4-triazol-1-yl)carbodithioate are stirred in 400 ml of 2-propanol, in the presence of 6.9 ml (0.13 mole) of methylhydrazine for 8 hours at room temperature. The separated crystals are filtered off and recrystallized from benzene.

Yield: 10.5 g (48%)
M.p.: 164° to 166° C.

EXAMPLE 6

1-(5-Amino-3-methylthio-1H-1,2,4-triazol-1-yl)-N-methyl-carbothiohydrazide 22.0 g (0.1 mole) of methyl (5-amino-3-methylthio-1H-1,2,4-triazol-1-yl)carbodithioate are stirred in 200 ml of benzene, in the presence of 6.9 ml (0.13 mole) of methylhydrazine for 8 hours at room temperature. The separated crystals are filtered off and recrystallized from benzene.

Yield: 8.9 g (41%)
M.p.: 164° to 166° C.

EXAMPLE 7

1-(5-Amino-3-methylthio-1H-1,2,4-triazol-1-yl)-N-methyl-carbothiohydrazide 22.0 g (0.1 mole) of methyl (5-amino-3-methylthio-1H-1,2,4-triazol-1-yl)carbodithioate are stirred in 150 ml of methanol, in the presence of 6.9 ml (0.13 mole) of methylhydrazine for 4 hours at room temperature. The separated crystals are filtered off and recrystallized from benzene.

Yield: 11.8 g (54%)
M.p.: 164° to 166° C.

EXAMPLE 8

1-(5-Amino-3-methylthio-1H-1,2,4-triazol-1-yl)-N-methyl-carbothiohydrazide 22.0 g (0.1 mole) of methyl (5-amino-3-methylthio-1H-1,2,4-triazol-1-yl)carbodithioate are boiled in 140 ml of methanol, in the presence of 5.7 ml (0.11 mole) of methylhydrazine for 1 hour. The reaction mixture is then evaporated to 70 ml, the separated crystals are filtered off and recrystallized from benzene.

Yield: 8.3 g (38%)
M.p.: 164° to 166° C.

EXAMPLE 9

1-[5-Amino-3-N-methylpiperazinyl)-1H-1,2,4-triazol-1-yl]-N-methyl-carbothiohydrazide 27.2 g (0.1 mole) of methyl (5-amino-3-N-methylpiperazinyl-1H-1,2,4-triazol-1-yl)carbodithioate are stirred in 150 ml of methanol, in the presence of 6.9 ml (0.13 mole) of methylhydrazine for 4 hours. The reaction mixture is evaporated to dryness in vacuo. The oily product thus obtained crystallises upon adding of 2-propanol. The separated crystals are filtered off and recrystallized from acetonitrile.

Yield: 13 g (48%)
M.p.: 150° to 152° C.

EXAMPLE 10

1-(5-Amino-3-dimethylamino-1H-1,2,4-triazol-1-yl)-N-methyl-carbothiohydrazide 21.7 g (0.1 mole) of methyl (5-amino-3-dimethylamino-1H-1,2,4-triazol-1-yl)carbodithioate are stirred in 100 ml of methanol, in the presence of 6.9 ml (0.13 mole) of methylhydrazine for 4 hours at room temperature. The separated crystals are filtered off and recrystallized from benzene.

Yield: 12.2 g (51%)
M.p.: 165° to 167° C.

EXAMPLE 11

1-(5-Amino-3-morpholino-4H-1,2,4-triazol-4-yl)-N-methyl-carbothiohydrazide 25.5 g (0.1 mole) of 1-(5-amino-3-morpholino-1H-1,2,4-triazol-1-yl)-N-methyl-carbodithiohydrazide are boiled in 75 ml of acetic acid for 30 minutes, under stirring. The reaction mixture is cooled, the separated crystals are filtered off and recrystallized from methanol.

Yield: 10.5 g (41%)
M.p.: 239° to 240° C.

EXAMPLE 12

1-(5-Amino-3-morpholino-2H-1,2,4-triazol-2-yl)-N-methyl-carbothiohydrazide

On proceeding as described in Example 11 the mother liquor obtained after filtering the reaction mixture is evaporated to dryness and the residue is recrystallized first from an aqueous ethanol solution then from acetonitrile.

Yield: 6.12 g (24%)
M.p.: 258° to 259° C.

EXAMPLE 13

2-Methyl-4-(3-morpholino-1H-1,2,4-triazol-5-yl)thiosemicarbazide 25.7 g (0.1 mole) of methyl (3-morpholino-2H-1,2,4-triazol-5-yl)dithiocarbaminate are boiled in 250 ml of methanol, in the presence of 6.9 ml (0.13 mole) of methylhydrazine for 2 hours, under stirring. The separated crystals are filtered off and recrystallized from methanol.

Yield: 17.34 g (68%)
M.p.: 211° to 212° C.

EXAMPLE 14

1-(5-Benzylamino-3-morpholino-1H-1,2,4-triazol-1-yl)-N-methyl-carbothiohydrazide 34.9 g (0.1 mole) of methyl (5-benzylamino-3-morpholino-1H-1,2,4-triazol-1-yl)carbodithioate are stirred in 150 ml of methanol, in the presence of 6.9 ml (0.13 mole) of methylhydrazine for 4 hours at room temperature. The separated crystals are filtered off and recrystallized from benzene.

Yield: 22.5 g (63%)
M.p.: 133° to 134° C.

EXAMPLE 15

1-(5-Benzylamino-3-morpholino-1H-1,2,4-triazol-1-yl)-N'-methyl-carbothiohydrazide One proceeds as described in Example 14, with the difference that the mother liquor obtained after filtration is allowed to stand for 2 days. Then the separated crystals are filtered off and recrystallized from a mixture of n-hexane and ether.

Yield: 5.6 g (16%)
M.p.: 86° to 87° C.

EXAMPLE 16

1-(5-Amino-3-morpholino-1H-1,2,4-triazol-1-yl)carbothiohydrazide

A mixture of 25.7 g (0.1 mole) of methyl (5-amino-3-morpholino-1H-1,2,4-triazol-1-yl)carbodithioate, 200 ml of methanol and 6 ml (0.12 mole) of a 99% hydrazine hydrate solution is stirred for 4 hours at room temperature. Then it is filtered and the thus-obtained crystals are recrystallized from a mixture of dimethylformamide and acetonitrile.

Yield: 20.9 g (86%)
M.p.: 180° to 182° C.

EXAMPLE 17

1-(5-Amino-3-methylthio-1H-1,2,4-triazol-1-yl)carbothiohydrazide

A mixture of 22.0 g (0.1 mole) of methyl (5-amino-3-methylthio-1H-1,2,4-triazol-1-yl)carbodithioate, 200 ml of methanol and 6 ml (0.12 mole) of a 99% hydrazine hydrate solution is stirred for 4 hours at room temperature. Then it is filtered and the precipitated crystals are recrystallized from dimethylformamide.

Yield: 17.3 g (85%)
M.p.: 185° to 186° C.

EXAMPLE 18

1-(5-Amino-3-methylthio-1H-1,2,4-triazol-1-yl)carbothiohydrazide

To a mixture of 10.6 g (0.1 mole) of thiocarbohydrazide and 130 ml of water a solution of 15 g (0.102 mole) of dimethyl (N-cyanocarbonimidodithioate) in 65 ml of methanol is added, and the reaction mixture is boiled for 2 hours. Then it is cooled, the precipitated crystals are filtered off and recrystallized from dimethylformamide.

Yield: 17.8 g (86%)
M.p.: 185° to 186° C.

EXAMPLE 19

1-[5-Amino-3-(N-methylpiperazinyl)-1H-1,2,4-triazol-1-yl]carbothiohydrazide 27.2 g (0.1 mole) of methyl [5-amino-3-(N-methylpiperazinyl)-1H-1,2,4-triazol-1-yl]carbodithioate are stirred in 150 ml of methanol, in the presence of 6.9 ml (0.13 mole) of hydrazine hydrate for 4 hours at room temperature. Then the reaction mixture is cooled and the thus-obtained crystals are recrystallized from dimethylformamide.

Yield: 24.5 g (94%)
M.p.: 194° to 196° C.

Preparation of the trihydrochloride salt 1 g of base obtained as described above is dissolved in 5 ml of hot dimethylformamide, and the solution is acidified to pH=2 with a 15% (v/v) solution of hydrogen chloride in isopropanol. The separated product is filtered off and washed with isopropanol.

Yield: 0.9 g
M.p.: 158° to 160° C.

EXAMPLE 20

1-(5-Amino-3-morpholino-1H-1,2,4-triazol-1-yl)-N,N'-dimethyl-carbothiohydrazide 25.7 g (0.1 mole) of methyl (5-amino-3-morpholino-1H-1,2,4-triazol-1-yl)carbodithioate are boiled in 150 ml of methanol, in the presence of 14.6 ml (0.12 mole) of N,N'-dimethylhydrazine dihydrochloride and 46 ml of triethylamine for 16 hours. Then the reaction mixture is evaporated to dryness in vacuo. 400 ml of water are added to the residue and the aqueous phase is extracted three times with 200 ml of chloroform. The organic phase thus obtained is washed two times with 200 ml of water, dried over magnesium sulfate and evaporated in vacuo. The precipitated crystals are suspended in diethyl ether and filtered off.

Yield: 11.3 g (43%)
M.p.: 127° to 128° C.

EXAMPLE 21

1-(5-Amino-3-diallylamino-1H-1,2,4-triazol-1-yl)-N-methyl-carbothiohydrazide 4.2 g (0.0156 mole) of methyl (5-amino-3-diallylamino-1H-1,2,4-triazol-1-yl)carbodithioate and 1.38 ml (0.026 mole) of methylhydrazine are reacted in 20 ml of methanol at room temperature for 8 hours. Upon adding 10 ml of water to the thus-obtained solution 1.2 g (29%) of pure 1-(5-amino-3-diallylamino-1H-1,2,4-triazol-1-yl)-N-methyl-carbothiohydrazide get separated. M.p.: 86° to 88° C. When evaporating the mother liquor further 2 g of crystalline product are obtained which melt at 85° to 88° C. So the total yield amounts to 77%.

EXAMPLE 22

1-(5-Benzylamino-3-morpholino-1H-1,2,4triazol-1-yl)-N,N'-dimethyl-carbothiohydrazide 6.98 g (0.02 mole) of methyl (5-benzylamino-3-morpholino-1H-1,2,4-triazol-1-yl)carbodithioate are boiled in 50 ml of methanol, in the presence of 2.92 ml (0.024 mole) of N,N'-dimethylhydrazine dihydrochloride and 9.4 ml of triethylamine for 8 hours. Then the reaction mixture is evaporated to dryness in vacuo. 100 ml of water are added to the residue and the aqueous phase is extracted three times with 50 ml of chloroform. The thus-obtained organic phase is washed twice with 50 ml of water, dried over magnesium sulfate and evaporated to dryness in vacuo. The thus-obtained crystals are suspended in diethyl ether and filtered off.

Yield: 3.25 g (45%)
M.p.: 66° to 68° C.

EXAMPLE 23

1-[5-(4-Dimethylaminobenzylamino)-3-morpholino-1H-1,2,4-triazol-1-yl]carbothiohydrazide 1.96 g (0.005 mole) of methyl [5-(4dimethylaminobenzylamino)-3-morpholino-1H-1,2,4-triazol-1-yl]carbodithioate are boiled in 20 ml of methanol, in the presence of 0.3 ml of hydrazine hydrate for 1 hour, under stirring. The reaction mixture is cooled, the separated crystals are filtered off and recrystallized from methanol.

Yield: 1.43 g (83%)
M.p.: 127° to 129° C.

EXAMPLE 24

1-(4-Chlorobenzylamino-3-morpholino-1H-1,2,4-triazol-1-yl)-N-methyl-carbothiohydrazide 38.2 g (0.1 mole) of methyl [5-(4-chlorobenzylamino)-3-morpholino-1H-1,2,4-triazol-1-yl]carbodithioate are boiled in 700 ml of methanol, in the presence of 6.4 ml (0.12 mole) of methylhydrazine for 1 hour, under stirring. The reaction mixture is cooled, the precipitated crystals are filtered off and recrystallized from a mixture of benzene and cyclohexane.

Yield: 23.2 g (61%)
M.p.: 152° to 154° C.

EXAMPLE 25

1-[5-(4-chlorobenzylamino)-3-methylthio-1H-1,2,4-triazol-1-yl]carbothiohydrazide 17.2 g (0.05 mole) of methyl [5-(4-chlorobenzylamino)-3-methylthio-1H-1,2,4-triazol-1-yl]carbodithioate are boiled in 200 ml of methanol, in the presence of 6 ml of hydrazine hydrate for 0.5 hour, under stirring. The reaction mixture is cooled, the separated crystals are filtered off and recrystallized from methanol.

Yield: 13.8 g (84%)
M.p.: 140° to 142° C.

EXAMPLE 26

1-(5-Benzylamino-3-morpholino-1H-1,2,4-triazol-1-yl)carbothiohydrazide 3.49 g (0.01 mole) of methyl (5-benzylamino-3-morpholino-1H-1,2,4-triazol-1-yl)carbodithioate are stirred in 50 ml of methanol, in the presence of 0.64 ml (0.013 mole) of hydrazine hydrate for 4 hours, at room temperature. The separated crystals are filtered off and recrystallized from methanol.

Yield: 2.84 g (85%)
M.p.: 141° to 143° C.

EXAMPLE 27

1-[5-(4-Chlorobenzylamino)-3-morpholino-1H-1,2,4-triazol-1-yl]carbothiohydrazide 1.9 g (0.005 mole) of methyl [5-(4-chlorobenzylamino)-3-morpholino-1H-1,2,4-triazol-1-yl]carbodithioate are boiled in 40 ml of methanol, in the presence of 0.3 ml (0.0058 mole) of hydrazine hydrate for 1 hour, under stirring. Then the separated crystals are filtered off and recrystallized from methanol.

Yield: 2.64 g (71%)
M.p.: 169° to 171° C.

EXAMPLE 28

1-(3,5-Diamino-1H-1,2,4-triazol-1-yl)-N-methylcarbothiohydrazide 0.76 g (0.004 mole) of methyl (3,5-diamino-1H-1,2,4-triazol-1-yl)-N-methyl-carbodithioate is stirred in 75 ml of methanol, in the presence of 0.29 ml of hydrazine hydrate for 1 hour at room temperature. The separated crystals are filtered off and recrystallized from 2-propanol.

Yield. 0.68 g (73%)
M.p.: 184° to 186° C.

EXAMPLE 29

1-(5-Amino-3-diallylamino-1H-1,2,4-triazol-1-yl)carbothiohydrazide 26.90 g (0.1 mole) of methyl-(5-amino-3-diallylamino-1H-1,2,4-triazol-1-yl)carbodithioate are boiled in 200 ml of methanol, in the presence of 6 ml of hydrazine hydrate for 1 hour, under stirring. The precipitated crystals are filtered off and recrystallized from benzene.

Yield: 20.64 g (82%)
M.p.: 142° to 144° C.

EXAMPLE 30

1-(5-Amino-3-methylthio-1H-1,2,4-triazol-1-yl)carbohydrazide

To a mixture of 9 g (0.1 mole) of carbohydrazide and 160 ml of methanol a solution of 14.6 g (0.102 mole) of dimethyl N-cyanocarbonimidodithioate in 100 ml of methanol is added under stirring. The reaction mixture is boiled for 3 hours, then it is cooled, the separated crystals are filtered off and recrystallized from methanol.

Yield: 15.6 g (83%)
M.p.: 163° to 164° C.

EXAMPLE 31

1-(5-Amino-2H-1,2,4-triazol-2-yl)-N-methylcarbothiohydrazide 0.61 g (0.0035 mole) of 1-(5-amino-2H-1,2,4-triazol-2-yl)carbodithioate is stirred in 10 ml of methanol, in the presence of 0.184 ml (0.004 mole) of methylhydrazine for 2 hours, at room temperature. The solution is evaporated to dryness in vacuo and the residue is recrystallized from isopropanol.

Yield: 0.4 g (66%)
M.p.: 85° to 90° C.

EXAMPLE 32

Tablets having the following composition are prepared by methods known per se of the pharmaceutical industry:

| Components | Amount, g/tablet |
| --- | --- |
| 1-(5-Amino-3-morpholino-1H-1,2,4-triazol-1-yl)carbothiohydrazide | 5 |
| Lactose | 18.5 |
| Potato starch | 13.0 |
| Polyvinylpyrrolidone | 6.8 |
| Stearic acid | 2.7 |
| Talc | 4.0 |
| Total weight | 50.0 g |

EXAMPLE 33

Ointments having the following composition are prepared by methods known per se of the pharmaceutical industry:

| Components | Amount |
| --- | --- |
| 1-(5-Amino-3-morpholino-1H-1,2,4-triazol-1-yl)-N-methyl-carbothiohydrazide | 500 mg |
| Unguentum hydrophilicium nonbonicum | 10 g |

The active ingredient is in the outer phase of the ointment, in dissolved state.

EXAMPLE 34

Suppositories having the following composition are prepared by methods known per se of the pharmaceutical industry:

| Components | Amount, mg/suppository |
| --- | --- |
| 1-(5-Amino-3-morpholino-1H- | 100 |

-continued

| Components | Amount, mg/suppository |
|---|---|
| 1,2,4-triazol-1-yl)carbothio-hydrazide | |
| Lecithin | 48 |
| Cera alba | 96 |
| Cocoa butter | 1870 |
| Distilled water | 386 |
| Total weight | 2500 mg |

EXAMPLE 35

Capsules having the following composition are prepared by methods known per se of the pharmaceutical industry:

| Components | Amount, mg/capsule |
|---|---|
| 1-(5-Amino-3-morpholino-1H-1,2,4-triazol-1-yl)carbothio-hydrazide | 50 |
| Lactose | |
| Potato starch | 10 |
| Magnesium stearate | 1 |
| Total weight | 180 mg |

What we claim is:

1. A triazolyl hydrazide derivative of the Formula (I) and a pharmaceutically acceptable salt thereof

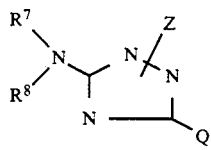 (I)

wherein

Q represents morpholino,

Z represents hydrogen or a group of the formula $-(C=X)-(N-R^4)-NR^5R^6$, wherein X stands for oxygen or sulfur;

$R^4$, $R^5$ and $R^6$ each stand for hydrogen or $C_{1-4}$ alkyl, $R^7$ stands for hydrogen, $C_{1-4}$ alkyl or phenyl-($C_{1-4}$ alkyl) optionally substituted by one or more halogen atom(s) or an amino group optionally substituted by one or two $C_{1-4}$ alkyl substituent(s); and $R^8$ stands for hydrogen or a group of the Formula $-(C=X)-(N-R^4)-NR^5R^6$, wherein X, $R^4$, $R^5$ and $R^6$ are as stated above; with the proviso that if Z represents a group of the formula $-(C=X)-(N-R^4)-NR^5R^6$, then $R^8$ stands for hydrogen, and if Z represents hydrogen, then $R^8$ stands for a group of the formula $-(C=X)-(N-R^4)-NR^5R^6$.

2. A pharmaceutical composition having antianginal and/or gastric ulcer inhibiting effect comprising as active ingredient at least one compound of the formula (I) of claim 1 or a pharmaceutically acceptable salt thereof in admixture with suitable inert solid or liquid pharmaceutical carriers, said active ingredient being present in said admixture in an effective amount required to exhibit an antianginal and/or gastric ulcer inhibiting effect.

3. A method of antianginal and/or gastric ulcer inhibiting treatment, which comprises administering to a patient a compound of the formula (I) of claim 1 or a pharmaceutically acceptable salt thereof, said compound or pharmaceutically acceptable salt of said compound being administered in an effective amount required to exhibit an antianginal effect and/or gastric ulcer inhibiting effect.

4. 1-(5-amino-3-morpholino-1H-1,2,4-triazol-1-yl)-carbothiohydrazide, and a pharmaceutically acceptable acid addition salt thereof.

* * * * *